United States Patent [19]

Burjes et al.

[11] Patent Number: 5,616,816

[45] Date of Patent: Apr. 1, 1997

[54] TERTIARY ALKYL ALKYLPHENOLS AND ORGANIC COMPOSITIONS CONTAINING SAME

[75] Inventors: Louis Burjes, Wickliffe; Calvin W. Schroeck, Willoughby Hills, both of Ohio

[73] Assignee: The Lubrizol Corporation, Wickliffe, Ohio

[21] Appl. No.: 457,345

[22] Filed: Jun. 1, 1995

Related U.S. Application Data

[62] Division of Ser. No. 962,382, Oct. 16, 1992.

[51] Int. Cl.$^6$ ................................................ C07C 39/23
[52] U.S. Cl. .................................... 568/727; 568/723
[58] Field of Search ............................................ 568/727

[56] References Cited

U.S. PATENT DOCUMENTS

| | | | |
|---|---|---|---|
| Re. 22,909 | 8/1947 | Smith et al. | 252/52 |
| 2,515,906 | 7/1950 | Stevens et al. | 260/619 |
| 2,538,355 | 1/1951 | Davis et al. | 260/45.95 |
| 2,570,402 | 10/1951 | Stevens et al. | 252/52 |
| 2,734,088 | 2/1956 | Knowles et al. | 260/619 |
| 2,792,428 | 5/1957 | Pikl | 260/619 |
| 2,796,444 | 6/1957 | Sullivan | 260/619 |
| 2,807,653 | 9/1957 | Filbey et al. | 260/619 |
| 2,809,164 | 10/1957 | Pruett | 252/51.5 |
| 2,830,025 | 4/1958 | Knowles et al. | 252/52 |
| 2,968,630 | 1/1961 | Pillon et al. | 252/403 |
| 3,017,443 | 1/1962 | Chenicek et al. | 260/810 |
| 3,055,862 | 9/1962 | Bentley | 260/45.95 |
| 3,068,198 | 12/1962 | Haines et al. | 260/45.95 |
| 3,407,140 | 10/1968 | Chiddix et al. | 252/47.5 |
| 3,462,392 | 8/1969 | Kaplan | 260/45.85 |
| 3,530,069 | 9/1970 | O'Neill | 252/46.4 |
| 3,554,945 | 1/1971 | Andress et al. | 252/52 |
| 3,694,374 | 9/1972 | Sparks et al. | 252/400 |
| 3,741,909 | 6/1973 | Yamane et al. | 252/401 |
| 4,066,562 | 1/1978 | Wollensak et al. | 252/52 |
| 4,070,304 | 1/1978 | Hinze | 252/404 |
| 4,087,469 | 5/1978 | Gurvich et al. | 568/723 |
| 4,115,355 | 9/1978 | Goto et al. | 260/45.95 |
| 4,243,539 | 1/1981 | Farcasiu et al. | 252/52 |
| 4,319,052 | 3/1982 | Styskin et al. | 568/727 |
| 4,322,527 | 3/1982 | Rasberger | 544/157 |
| 4,386,204 | 5/1983 | Rasberger | 546/21 |
| 4,409,346 | 10/1983 | Rasberger | 524/83 |
| 4,525,514 | 1/1985 | Yachigo et al. | 524/291 |
| 4,707,300 | 11/1987 | Sturm et al. | 252/404 |
| 4,914,246 | 4/1990 | Oswald et al. | 568/793 |

FOREIGN PATENT DOCUMENTS

| | | |
|---|---|---|
| 497039 | 12/1950 | Belgium. |
| 480524 | 1/1952 | Canada. |
| 0003338 | 8/1979 | European Pat. Off. |
| 0020297 | 12/1980 | European Pat. Off. |
| 1294583 | 4/1960 | Germany. |
| 928169 | 12/1960 | United Kingdom. |
| 927179 | 5/1963 | United Kingdom. |

OTHER PUBLICATIONS

"Alkylphenols" in Kirk–Othmer Encyclopedia of Chemical Technology, 3rd Ed., vol. 2, pp. 82–83, 92 (1978).
Chemical Abstracts 109: 180376C re JP 6350850 (1988).
Chemical Abstracts 110: 2326175 re JP 63238164 (1989).
Chemical Abstracts, 9th Collective Index, Chemical Substances, Columbus, Ohio (Page 27867 CS.) (1978).
Chemical Abstracts, vol. 115 (1991), Abstract No. 194126g.
Chemical Abstracts, vol. 69 (1968), Abstract No. 1844q.
Chemical Abstracts, vol. 86, No. 13, 28 Mar. 1977, Columbus, Ohio, Abstract No. 89373u, p. 502, column 2.
J. A. M. Laan and J. P. Ward, "Selective Mono–ortho Alkylation of Phenol With an Aluminum Catalyst," Chemistry and Industry, 5 Jan. 1987, pp. 34–35.
G. A. Olah et al, Nafion–H Catalyzed De–tert–butylation of Aromatic Compounds, in J. Org. Chem., 52, (1987), pp. 1881–1884.
G. A. Olah, Alkylation of Aromatics with Alkenes and Alkanes, in Friedel–Crafts and Related Reactions, Interscience (NY), (1964), pp. 75–86, 199–201, 204–208.
Royals, E. E., of Advanced Organic Chemistry, 1954, pp. 86–90. 1954.

*Primary Examiner*—Porfirio Nazario-Gonzalez
*Assistant Examiner*—Dwayne C. Jones
*Attorney, Agent, or Firm*—Joseph P. Fischer; Frederick D. Hunter; James L. Cordek

[57] ABSTRACT

Novel compounds of the general formula

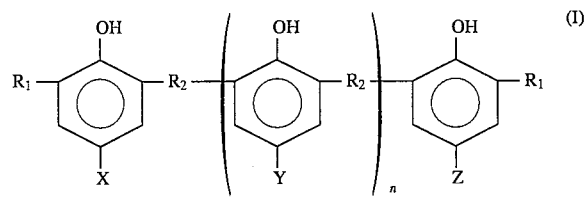

wherein each $R_1$ is independently a tertiary alkyl group containing from 4 to about 8 carbon atoms and each of X, Y and Z is independently hydrogen or a hydrocarbon-based group, provided at least one of X, Y and Z is an aliphatic hydrocarbon group containing at least 7 carbon atoms, and wherein $R_1$ is different from the at least one of X, Y and Z that is an aliphatic hydrocarbon group containing at least 7 carbon atoms, $R_2$ is an alkylene or alkylidene group, and n is a number ranging from zero to about 4. Also disclosed are methods for preparing novel phenolic compounds, organic compositions, including lubricants based on oils of lubricating viscosity and fuels based on normally liquid fuels and additive concentrates containing the novel phenolic compounds of this invention.

24 Claims, No Drawings

TERTIARY ALKYL ALKYLPHENOLS AND ORGANIC COMPOSITIONS CONTAINING SAME

This is a divisional of copending application Ser. No. 07/962,382 filed Oct. 16, 1992.

FIELD OF THE INVENTION

This invention relates to phenolic compounds, particularly phenolic compounds employed as antioxidants for organic compositions, more particularly for lubricating oil compositions and normally liquid fuel compositions.

BACKGROUND OF THE INVENTION

Organic materials are often susceptible to oxidation, resulting in undesirable effects such as objectionable odor, sludge formation, loss of strength, development of or increased acidity, and the like.

Numerous compounds have been found to reduce oxidative susceptibility of various organic materials. Well known antioxidant compounds include various divalent sulfur-containing compounds, certain aromatic amines and phenolic compounds and derivatives. Certain hindered phenolic compounds have been described as being particularly suitable as antioxidants for organic materials, especially on a cost-performance basis. However, not all compounds of this type provide antioxidancy. Furthermore, numerous compounds of this type possess other properties which are objectionable. It is also desirable that lubricating and fuel compositions are essentially free of chlorine. Preferably, they contain no chlorine.

Davis, et al in U.S. Pat. No. 2,538,355 describes 2,2'-alkylene bis-4,6-dialkyl phenols of the formula

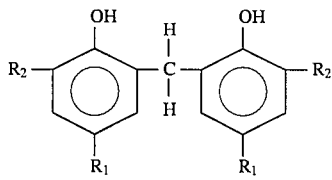

wherein $R_1$ is a straight chain alkyl radical of from 1 to 3 carbon atoms and $R_2$ is a tertiary alkyl radical of from 4 to about 8 carbon atoms as rubber stabilizers.

Stevens et al in U.S. Pat. No. 2,515,906 describes bis(hydroxyphenyl) compounds of the formula

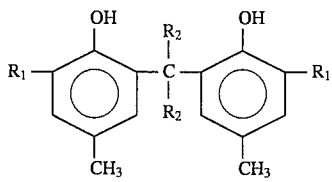

wherein $R_1$ is selected from the class consisting of secondary and tertiary butyl groups and $R_2$ is selected from the class consisting of alkyl, cycloalkyl, aryl, aralkyl and alkaryl groups as additives for oil. In U.S. Pat. No. 2,570,402, Stevens et al describes oils and gasolines containing these compounds.

Knowles et al in U.S. Pat. No. 2,830,025 describes lubricating compositions containing monomeric condensation products of alkylated phenols with carbonyl-containing compounds. The condensation products are represented by the formulae

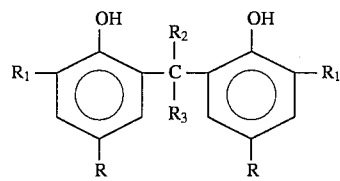

and

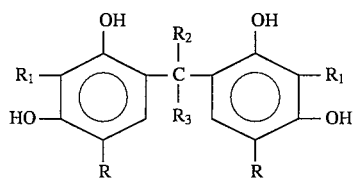

wherein R is a hydrocarbon radical which may be alkyl, aryl, aralkyl or alkaryl, $R_1$ is tertiary alkyl, $R_2$ is a hydrogen or an alkyl radical and $R_2$ is a hydrocarbon radical such as R. R is preferably alkyl having from 1 to 12 carbons, $R_2$ is tertiary alkyl containing 4 to 12 carbons, $R_2$ is hydrogen or methyl and $R_3$ is preferably alkyl or halogenated alkyl having up to 7 carbon atoms.

It has been found that in certain applications, many of the bis-t-alkyl phenols of the art are ineffective or only marginally effective. Lubricating oils require antioxidants that are soluble or dispersable in oil in amounts effective to provide antioxidancy. High temperature applications require additives that are stable at the elevated temperatures and which are substantially non-volatile under conditions of use. By substantially non-volatile is meant that at least 50%, preferably at least 75% and more preferably at least 90% by weight of the additive remains in the lubricant under conditions of use.

For fuels, solubility in the fuel is also required.

For use in other applications such as resins, rubbers, waxes, etc. it is generally desirable that the compounds do not impart pronounced color to the substrate and also are substantially non-volatile.

Therefore, it is an object of this invention to provide novel phenolic compositions that will impart useful and desirable properties to organic materials.

It is a further object of this invention to provide novel organic compositions containing the novel phenolic compositions of this invention.

A further object is to provide novel lubricant and fuel compositions containing the novel phenolic compounds of this invention.

Other objects will be apparent to those skilled in the art upon review of the present specification.

SUMMARY OF THE INVENTION

The objects of this invention are accomplished by providing novel compounds of the general formula

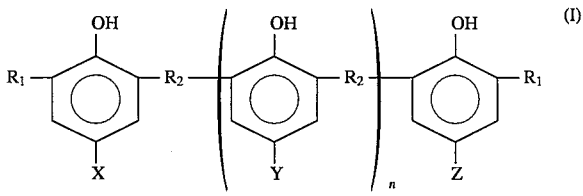

wherein each $R_1$ is independently a tertiary alkyl group containing from 4 to about 8 carbon atoms and each of X, Y and Z is independently hydrogen or a hydrocarbon-based group, provided at least one of X, Y and Z is an aliphatic hydrocarbon group containing at least 7 carbon atoms, and wherein $R_1$ is different from the at least one of X, Y and Z that is an aliphatic hydrocarbon group containing at least 7 carbon atoms, $R_2$ is an alkylene or alkylidene group, and n is a number ranging from zero to about 4.

Methods for preparing novel phenolic compounds are also provided. Organic compositions, including lubricants based on oils of lubricating viscosity and fuels based on normally liquid fuels are within the scope of this invention. Additive concentrates containing the novel phenolic compounds of this invention also are within the scope of this invention.

DETAILED DESCRIPTION OF THE INVENTION

As used herein, the terms "hydrocarbyl" "hydrocarbon-based", "hydrocarbon" or "hydrocarbyl group" are, unless otherwise indicated, used interchangeably, and denote a group having a carbon atom directly attached to the remainder of the molecule and having predominantly hydrocarbon character within the context of this invention. Thus, these terms include hydrocarbon, as well as substantially hydrocarbon groups. Substantially hydrocarbon describes groups, including hydrocarbon based groups which contain non-hydrocarbon substituents, or non-carbon atoms in a ring or chain which do not alter the predominantly hydrocarbon nature of the group.

Hydrocarbyl groups can contain up to three, preferably up to two, more preferably up to one, non-hydrocarbon substituent, or non-carbon heteroatom in a ring or chain, for every ten carbon atoms provided this non-hydrocarbon substituent or non-carbon heteroatom does not significantly alter the predominantly hydrocarbon character of the group. Those skilled in the art will be aware of such heteroatoms, such as oxygen, sulfur and nitrogen, or substituents, which include, for example, hydroxyl, halo (especially chloro and fluoro), alkyoxyl, alkyl mercapto, alkyl sulfoxy, etc.

Examples of hydrocarbyl groups include, but are not necessarily limited to, the following:

(1) hydrocarbon groups, that is, aliphatic (e.g., alkyl or alkenyl), alicyclic (e.g., cycloalkyl, cycloalkenyl) groups, aromatic groups (e.g., phenyl, naphthyl), aromatic-, aliphatic- and alicyclic-substituted aromatic groups and the like as well as cyclic groups wherein the ring is completed through another portion of the molecule (that is, for example, any two indicated groups may together form an alicyclic radical);

(2) substituted hydrocarbon groups, that is, those groups containing non-hydrocarbon containing substituents which, in the context of this invention, do not significantly alter the predominantly hydrocarbon character; those skilled in the art will be aware of such groups (e.g., halo (especially chloro and fluoro), hydroxy, alkoxy, mercapto, alkylmercapto, nitro, nitroso, sulfoxy, etc.);

(3) hetero atom containing groups, that is, groups which will, while having a predominantly hydrocarbon character within the context of this invention, contain atoms other than carbon present in a ring or chain otherwise composed of carbon atoms. Suitable heteroatoms will be apparent to those of ordinary skill in the art and include, for example, sulfur, oxygen, nitrogen. Such groups as, e.g., pyridyl, furyl, thienyl, imidazolyl, etc. are representative of heteroatom containing cyclic groups.

Typically, no more than about 2, preferably no more than one, non-hydrocarbon substituent or non-carbon atom in a chain or ring will be present for every ten carbon atoms in the hydrocarbyl group. Usually, however, the hydrocarbyl groups are purely hydrocarbon and contain substantially no such non-hydrocarbon groups, substituents or heteroatoms.

Unless indicated otherwise, hydrocarbyl groups may be saturated or unsaturated. Saturated groups include those which are substantially saturated. By substantially saturated it is meant that the group contains no more than one carbon-to-carbon unsaturated bond, olefinic unsaturation, for every ten carbon-to-carbon bonds present. Often, they contain no more than one carbon-to-carbon non-aromatic unsaturated bond for every 50 carbon-to-carbon bonds present. Frequently, hydrocarbyl groups are substantially free of carbon to carbon unsaturation. It is to be understood that, within the context of this invention, aromatic unsaturation is not normally considered to be olefinic unsaturation. That is, aromatic groups are not considered as having carbon-to-carbon unsaturated bonds.

The phenolic compounds of this invention have the general formula

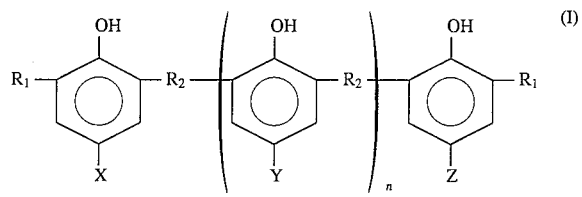

(I)

wherein each $R_1$ is independently a tertiary alkyl group containing from 4 to about 8 carbon atoms and each of X, Y and Z is independently hydrogen or a hydrocarbon-based group, provided at least one of X, Y and Z is an aliphatic hydrocarbon group containing at least 7 carbon atoms, and wherein $R_1$ is different from the at least one of X, Y and Z that is an aliphatic hydrocarbon group containing at least 7 carbon atoms, $R_2$ is an alkylene or alkylidene group, and n is a number ranging from zero to about 4.

Each $R_1$ group must be a tertiary alkyl group. Tertiary alkyl groups have the general structure

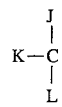

wherein each of J, K and L is an alkyl group. Representative tertiary alkyl groups are tertiary butyl, tertiary amyl, tertiary hexyl and tertiary octyl. The $R_1$ groups may be the same or different. Preferably all $R_1$ are the same, more preferably, they are all tertiary butyl groups.

Each $R_2$ is independently a divalent group such as an alkylene or an alkylidene group. These groups may be substituted, for example, by various hydrocarbyl groups such as alkyl and aryl groups. Representative examples of suitable $R_2$ groups are methylene, ethylene, propylene, phenyl substituted methylene, methyl substituted methylene, methyl-ethylene and the like. Typically, each $R_2$ contains from one to about 10 carbon atoms, preferably from one to about three carbon atoms. In one preferred embodiment, $R_2$ is phenyl substituted methylene. In a most preferred embodiment, each $R_2$ is methylene, that is, a group of the formula —$CH_2$—.

Each of X, Y and Z is, independently hydrogen or a hydrocarbon-based group. At least one of X, Y and Z is an aliphatic hydrocarbon group containing at least 7 carbon atoms, preferably from at least 7 up to about 100 carbon atoms.

In one particularly preferred embodiment, each of X, Y and Z is, independently, an aliphatic hydrocarbon group, at least one containing at least 7 carbon atoms, up to about 100 carbon atoms.

In another preferred embodiment, at least one of X, Y and Z is, independently, an aliphatic hydrocarbon group containing from about 8 to about 30 carbon atoms, preferably from 12 to about 18 carbon atoms.

In a further embodiment, at least one of X, Y and Z is, independently, an aliphatic hydrocarbon group containing from 18 to about 50 carbon atoms, preferably from 18 to about 30 carbon atoms, often from about 22 to about 28 carbon atoms.

In still another embodiment, at least one of X, Y and Z is, independently, an aliphatic hydrocarbon group containing at least about 30, often at least about 50 carbon atoms, up to about 300, more preferably up to about 200 and more often up to about 100 carbon atoms.

As mentioned hereinabove, in one particularly preferred embodiment, each of X, Y and Z is, independently, an aliphatic hydrocarbon group. These groups may be the same or different. Within the aforementioned constraints that at least one of X, Y and Z is an aliphatic hydrocarbon group containing at least 7 carbon atoms, the others may be alkyl or alkenyl, preferably alkyl. Thus each of these groups will contain at least one carbon atom, but may contain more. Preferably they contain from one to about 500 carbon atoms, preferably from 4 to about 100 carbon atoms, often from about 4 to about 30 carbon atoms. These groups also frequently contain at least about 7, more often at least about 8, frequently at least about 12 and frequently at least about 18 carbon atoms, up to about 100 carbons, preferably up to about 50 carbon atoms, often up to about 30 carbon atoms and frequently up to about 18 carbon atoms. As mentioned hereinabove, at least one of X, Y and Z must be an aliphatic hydrocarbon group containing at least 7 carbon atoms.

In another embodiment, within the constraints that at least one of X, Y and Z is an aliphatic hydrocarbon group containing at least 7 carbon atoms, the other members of X, Y and Z may be hydrogen or other than purely aliphatic groups. For example, they may be aryl, aralkyl or alkaryl groups. Illustrative examples include, but are not limited to, hydrogen, phenyl, alkyl substituted phenyl, phenyl substituted alkyl, alkyl substituted naphthyl, etc., hetero atom containing groups such as pyridyl, thienyl, etc.

In a further embodiment, within the constraints that at least one of X, Y and Z is independently an aliphatic hydrocarbon group containing at least 7 carbon atoms, the remaining members may be a mixture of aliphatic hydrocarbon groups and groups that are not purely aliphatic such as those illustrated hereinabove. These mixtures may include those wherein at least one of X, Y or Z is hydrogen.

As indicated hereinabove, it is desirable for high temperature applications that the phenolic antioxidant is substantially non-volatile under conditions of use. Another important consideration is compatibility of the phenolic compound with the other components of the composition in which it is employed. The phenolic compound must display antioxidant properties.

An important compatibility issue is the solubility of the compound in the substrate (e.g., resin, oil, fuel, etc.) in which it is being used. It is generally important that the phenolic compound is soluble in or readily dispersible in, the organic substrate. By soluble or readily dispersible is meant that at least about 1 part by weight of the phenolic compound is soluble or readily dispersible in 10000 parts by weight of the organic composition (substrate). Preferably, at least 5 parts, more preferably at least 10 parts, even more preferably at least 100 parts of the phenolic compound is soluble in or can be readily dispersed in 10000 parts of the organic substrate. It is particularly important that the phenolic compound remains soluble or uniformly dispersed in the substrate under anticipated conditions of storage and use.

Under certain conditions, such as low temperatures, the presence of groups having a wax-like character may result in significant low-temperature incompatibility problems. Occasionally, such difficulties may be overcome by the use of pour point depressants (discussed in greater detail hereinafter). Also, waxy materials can sometimes be used as cold flow improvers and pour point depressants in compositions which contain other materials having a wax-like character.

"Waxy" character is often associated with carbon compounds having long chains (e.g., at least 8 carbons, often at least 12 carbons) which have little or no hydrocarbon branching. In a preferred embodiment, the groups X, Y and Z are substantially free of (i.e. contain less than 50%, preferably less than 25%, more preferably less than 5%, most preferably less than 1%) carbon atoms in an unsubstituted straight chain configuration, wherein the straight chain contains more than 10 carbon atoms. More preferably, the straight chain does not contain more than 4 carbon atoms.

The subscript "n" is a number ranging from 0 to about 4. Thus, when n is a number greater than 0, the phenolic compound of this invention will contain one or more groups of the formula

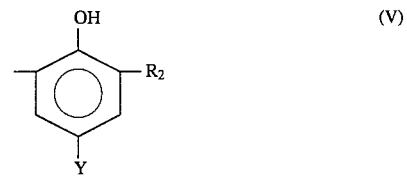

wherein $R_2$ and Y are as defined hereinabove. When n is a number greater than 1, there is more than one group of formula (V). In this case, there is more than one group Y. Each Y is independently hydrogen or a hydrocarbyl group as defined hereinabove, within the constraints that at least one of X, Y and Z is an aliphatic hydrocarbon group containing at least 7 carbon atoms.

In one preferred embodiment n equals about 1 and Y is hydrogen or an aliphatic hydrocarbon group, preferably an alkyl group. Preferred groups Y are those discussed hereinabove.

In another preferred embodiment, at least one group Y has the general formula

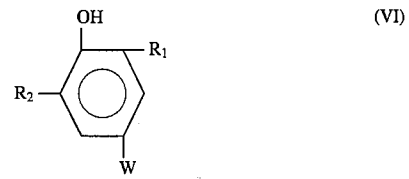

wherein W is a hydrocarbyl group, preferably an aliphatic group, more preferably an alkyl group, and $R_1$ and $R_2$ are as defined hereinabove. In one particularly preferred embodiment, n equals about 1 and each Y is independently a group of formula (VI).

In another preferred embodiment n equals zero; then X and Z are each as defined hereinabove and Y is absent.

Examples of phenolic compounds of the type represented by Formula (I) include 2,2'-methylene-bis(6-t-butyl-4-heptyl phenol); 2,2'-methylene-bis(6-t-butyl-4-octyl phenol); 2,2'-methylene-bis-(4-dodecyl-6-t-butyl phenol); 2,2'-methylene-bis-(4-octyl-6-t-amyl phenol); 2,2'-methylene-bis-(4-octyl-6-tertiary octyl phenol); 2,2'-methylene-bis-(4-dodecyl-6-tertiary amyl phenol); 2,2'-methylene-bis-(4-heptyl-6-tertiary octyl phenol); 2,2'-methylene-bis-(6-t-butyl-4-octadecyl phenol); 2,2'-methylene-bis(6-t-butyl-4-polybutenyl phenol), 1,2-di(2-hydroxy-5-dodecyl-3-t-butyl phenyl) ethane, 1,1-di(2-hydroxy-5-octadecyl-3-t-amyl phenyl) propane, 2,2'-phenylmethylene-bis(4-tetrapropenyl-6-t-butyl phenol), 2-(3,5-di-t-butyl-2-hydroxy phenyl), 2-(3-t-butyl-5-polybutenyl(1000)-2-hydroxy phenyl) methane and others.

The word "tetrapropenyl" is sometimes used herein to refer to a substituent on a phenolic compound, including reactants and compounds of this invention. It is not intended that the use of the word "tetrapropenyl" refers to a group containing olefinic unsaturation. The word "tetrapropenyl" as used herein refers to groups that are derived from propylene tetramer. These are highly branched, dodecyl groups.

When n=1, the compound of Formula (I) has the general structure

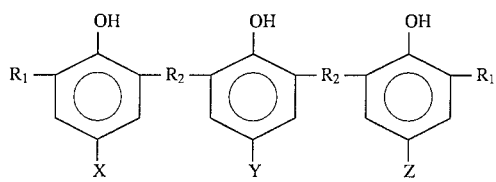

wherein each of $R_1$, $R_2$ and X, Y and Z is as defined hereinabove. Illustrative examples of these compounds are those in the following table:

| $R_1$ | $R_2$ | X | Y | Z |
|---|---|---|---|---|
| t-butyl | methylene | t-butyl | tetrapropenyl | t-butyl |
| t-butyl | $CH_3CCH_3$ | t-butyl | octadecyl | t-butyl |
| t-octyl | methylene | methyl | polyisobutenyl (1000) | methyl |
| t-butyl | methylene | tetrapropenyl | tetrapropenyl | tetrapropenyl |
| t-butyl | methylene | tetrapropenyl | $\begin{array}{c} CH_2 \\ | \\ \text{OH} \\ C_{12} \quad \text{t-Butyl} \end{array}$ | tetrapropenyl |
| t-butyl; t-amyl | methylene | octyl | n-$C_{22-30}$ alkyl | octyl |
| t-butyl | methylene | heptyl | octadecenyl | heptyl |
| t-butyl | methylene | hydrogen | polypropenyl (1000) | hydrogen |

When n is greater than 1, compounds analogous to those described above are obtained.

The phenolic compounds of this invention may be prepared by reacting at a temperature ranging from about 25° C. to about 200° C., preferably from about 80° C. to about 150° C., more preferably from about 100 ° C. to about 135° C., in the presence of an acidic catalyst, a phenol or a mixture of phenols of the formula

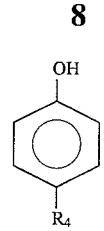

wherein at least about 50% of the $R_4$ groups are aliphatic hydrocarbon groups containing at least 7 carbon atoms with an olefin of the formula

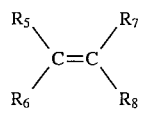

wherein each of $R_5$–$R_8$ is independently H or an alkyl group with the proviso that at least both of $R_5$ and $R_6$ or both of $R_7$ and $R_8$ are alkyl and the total number of carbon atoms in the olefin does not exceed 8, and wherein the molar ratio of (II) to (III) ranges from about 1:0.95 to about 1:1.2, and then reacting the product obtained thereby, in the presence of an acidic catalyst or a basic catalyst wherein the basic catalyst is selected from the group consisting of alkali and alkaline earth metal oxides, hydroxides and alkoxides, wherein the alkaline earth metal is selected from the group consisting of calcium, barium and strontium, with an aldehyde or ketone wherein the molar ratio of (II) to aldehyde or ketone ranges from about 2:1.8 to about 2:0.9 at temperatures ranging from about 25° C. to about 200° C., preferably from about 80° C. to about 150° C., more preferably from about 100° C. to about 135° C., and recovering the product obtained thereby. Preferred basic catalysts are alkali metal compounds, more preferably sodium and potassium oxides, hydroxides and alkoxides, more preferably, oxides and hydroxides, most preferably sodium hydroxide.

The attachment of a hydrocarbyl group $R_4$ to the aromatic moiety of the phenol (II) can be accomplished by a number of techniques well known to those skilled in the art. One particularly suitable technique is the Friedel-Crafts reaction, wherein an olefin (e.g. a polymer containing an olefinic bond), or halogenated or hydrohalogenated analog thereof, is reacted with a phenol. The reaction occurs in the presence of a Lewis acid catalyst (e.g., boron trifluoride and its complexes with ethers, phenols, hydrogen fluoride, etc., aluminum chloride, aluminum bromide, zinc dichloride). Methods and conditions for carrying out such reactions are well known to those skilled in the art. See, for example, the discussion in the article entitled, "Alkylation of Phenols" in Kirk-Othmer "Encyclopedia of Chemical Technology", Second Edition, Vol. 1, pages 894–895, Interscience Publishers, a division of John Wiley and Company, New York, 1963. Other equally appropriate and convenient techniques for attaching the hydrocarbon-based group $R_4$ to the aromatic moiety will occur readily to those skilled in the art.

In one embodiment, from about 25% up to about 50% of the $R_4$ groups of reactant (II) are hydrogen.

Once the reaction with the aldehyde or ketone is completed, it is common to neutralize the catalysts remaining in the product. The acidic catalyst may be neutralized with a basic material selected from the group consisting of basic metal compounds, ammonia and amines. Basic catalysts may be neutralized by reaction with no more than an equivalent amount of acid.

Acidic catalysts may be selected from a wide variety of acidic compounds. Especially preferred are strong acids such as phosphoric, sulfuric, sulfonic, hydrochloric and the like. The acid may be present as a component of a solid material such as acid treated clay, such as Super Filtrol and acidic resins such as Amberlyst 15 (Rohm & Haas).

Super Filtrol and commercial grade sulfuric acid (e.g. 93% $H_2SO_4$) are preferred. $H_2SO_4$, especially 93% $H_2SO_4$, is especially preferred.

Several of the acidic catalysts contain water. They may be dried prior to use, if desired, but it is not absolutely necessary to do so. In particular, drying of wet acidic catalysts in-situ with t-alkyl group containing phenolic reactants should be avoided since considerable de-t-alkylation may occur.

The amount of catalyst employed may vary over a relatively wide range, for example, from about 0.05 to 10% or more by weight of the total reaction mixture. Typically, the amount of catalyst ranges from about 0.1 to about 3% by weight, more preferably from about 0.2–1%, more preferably from about 0.3 to about 0.6%, based on the amount of active catalyst compound.

By active catalyst is meant the amount of chemical present. For examples, sodium hydroxide is often used as a 50% aqueous solution. The amount of sodium hydroxide is one-half of the weight of the 50% aqueous solution. Similarly, acid treated clays such as Super Filtrol contain only a portion of the total weight as active catalyst agent.

The aldehyde or ketone reactants for use in the foregoing process may be aliphatic or aromatic. The aliphatic reactants have the general formula

and the aromatic compounds have the general formula

wherein $R_x$ is H or an aliphatic hydrocarbon group containing from 1 to about 10 carbon atoms, preferably from 1 to about 4 carbon atoms. Most preferably $R_x$ is H or methyl.

Ar is an aromatic group, preferably phenyl or naphthyl, most preferably phenol.

When the reactant is an aldehyde, $R_y$ is hydrogen. When the reactant is a ketone $R_y$ is an aliphatic hydrocarbon group containing from 1 to about 10 carbon atoms, preferably from 1 to about 4 carbon atoms, most preferably, one carbon atom.

Examples of ketones useful in the process of this invention are acetone, methyl ethyl ketone, methyl isobutyl ketone, phenyl methyl ketone and the like.

Examples of useful aldehydes are formaldehyde (derived from, for example, 37% aqueous formaldehyde, paraformaldehyde, and the like), acetaldehyde, isobutyraldehyde, benzaldehyde, and the like.

Aldehydes are preferred reactants for use in coupling the phenolic reagents in the foregoing process. Formaldehyde is especially preferred.

It is desirable to maximize the amount of 4-alkyl phenol for coupling with the aldehyde or ketone. One means for accomplishing this is to react, in the presence of an acidic catalyst, a compound of the formula

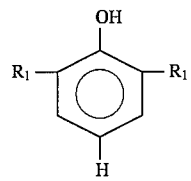

wherein each $R_1$ is independently a tertiary alkyl group containing from 4 to about 8 carbon atoms with an olefin containing at least 7 carbon atoms, or with a mixture of olefins wherein at least about 50 mole percent of the olefin contain at least 7 carbon atoms, to alkylate the phenol (IV) in the 4-position, then heating at an elevated temperature sufficient to cause partial de-t-alkylation by removal of one $R_1$ and then reacting the product obtained thereby, in the presence of an acidic catalyst or a basic catalyst wherein the basic catalyst is selected from the group consisting of alkali and alkaline earth metal oxides, hydroxides and alkoxides, and wherein the alkaline earth metal is selected from the group consisting of calcium, barium and strontium, with an aldehyde or ketone wherein the molar ratio of (IV) to aldehyde or ketone ranges from about 2:1.8 to about 2:0.9, at temperatures ranging from about 25° C. to about 200° C., and recovering the product obtained thereby.

Alkylation of the compound of Formula (IV) with an olefin is accomplished by conducting the reaction at the lowest possible temperature consistent with acceptable conversion and reaction times. Typically, this reaction will be conducted at temperatures ranging from about 25° C. to about 150° C., preferably from about 100° C. to about 150° C., more preferably from about 80° C. to about 120° C. Temperatures above about 160° C. should be avoided since above such temperatures, significant de-t-alkylation occurs and the selective alkylation with the olefin (III) at the 4-position will be impaired, with significant alkylation taking place at vacant 2- or 6- positions of the aromatic ring arising from the de-t-alkylation.

Once the desired extent of alkylation at the 4-position is completed, the temperature of the reaction mass is increased to at least 100° C. up to the temperature at which adverse decomposition of components of the reaction mass occurs. This heating at an elevated temperature results in the loss of a t-alkyl group from the 2,6-t-alkyl phenol. Preferred temperatures for this de-t-alkylation reaction range from about 100° C. to about 200° C., more preferably from 135° C. to about 150° C. The extent of de-t-alkylation can be conveniently followed by infrared analysis until the desired extent of mono-de-t-alkylation has occurred. Desirably, at least 90% de-t-alkylation occurs, preferably at least 95% since it is desired that coupling of the phenol at a position ortho to the hydroxy group is maximized.

The subsequent reaction of the substantially 2-t-alkyl phenol with an aldehyde or ketone is conducted at temperatures ranging from about 25° C. to about 200° C., preferably from 80° C. to about 150° C., more preferably from 100° C. to about 135° C. The reaction may take place in the presence of an acidic or basic catalyst. Useful catalysts and aldehyde and ketone reactants are the same as those described hereinabove. Preferred catalysts are those enumerated hereinabove.

In order to obtain compounds of Formula (I) where the subscript "n" is not zero, the reaction mixtures during reaction with the aldehyde or ketone must contain, in addition to the 2-t-alkyl phenol, phenols wherein both ortho- (2- and 6-) positions are vacant.

Likewise, it will be apparent that to obtain compounds of Formula (I) wherein at least one of X, Y and Z is hydrogen, the reaction mixture will contain phenolic reactants that have unsubstituted para- (4-) positions.

Thus, in one embodiment, from about 25% to about 50% of the intermediate derived from the phenol (IV) may be replaced with an equivalent amount, based on % OH, of a phenolic compound of formula

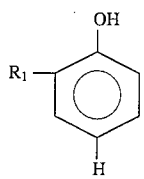

wherein the molar ratio of total phenolic compounds to aldehyde or ketone ranges from about 2:1.8 to about 2:0.9.

In another embodiment, from about 25 to about 50% of the intermediate derived from the phenol (IV) is replaced with an equivalent amount, based on % OH, of a compound having the formula

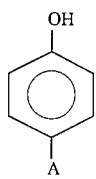

wherein A is H or hydrocarbyl and the molar ratio of total phenolic compounds to aldehyde or ketone ranges from about 2:1.8 to about 2:0.9.

The following Examples are provided to illustrate the compounds of this invention and methods for preparing same. These Examples are intended to be illustrative only and are not intended to be limiting upon the scope of the invention. All temperatures are in degrees Celsius, all pressures are atmospheric unless indicated otherwise and all parts and percentages are by weight.

EXAMPLE 1

Part 1

A reactor equipped with a stirrer, thermometer, a water-cooled reflux condenser vented to a dry ice/acetone cooled condenser, a Dean-Stark trap and a submerged gas inlet tube is charged with 798 parts of 4-tetrapropenyl phenol. The contents are heated with stirring to 95°–100° C. over 0.5 hours then 5 parts of 93% $H_2SO_4$ is charged. Isobutylene is then added via the submerged gas inlet tube at 2 standard cubic feet per hour (SCFH) for 1.7 hours at 100° C. until 168 parts isobutylene have been added. The mixture is blown with nitrogen gas at 2 SCFH for 0.5 hours at 100° C.

Part II

A reactor equipped with a stirrer, thermometer, water-cooled reflux condenser, Dean-Stark trap and submerged gas inlet tube is charged with 890 parts of the reaction product from Part I. The materials are heated to 34°–40° C. followed by rapid addition of 137 parts 37% aqueous formaldehyde. The temperature increases exothermically to 54°–55° over 5 minutes. The reaction mixture is heated to 135° while removing water. When the temperature has reached 105°–110° C. nitrogen blowing is begun at 1.5 SCFH to aid in removal of water. The materials are held at 120° C. for 3 hours with nitrogen blowing at 1.5 SCFH. The materials are cooled to 83° C. followed by the addition of 4 parts 50% aqueous NaOH. The mixture is heated to 135° C. with nitrogen blowing at 2 SCFH followed by vacuum stripping at 135° C. and 20 millimeters mercury for 10 minutes. The residue is cooled to 95° C. under vacuum, them filtered with a diatomaceous earth filter aid at 100° C. Gel permeation chromatography (GPC) of the filtrate shows a $\overline{M}w$ of 693 and a $\overline{M}n$ of 591. Percent hydroxyl by Grignard analysis is 5.47 (5.5 theory).

EXAMPLE 2

Part I

To a reactor equipped as described in Part I of Example 1 are charged 4770 parts of a 4-tetrapropenylphenol. The materials are heated to 40° C. at which time 298 parts Super Filtrol (acid treated clay—Filtrol Corporation) is charged. The materials are dried by heating the mixture to 105°–110° C. with nitrogen blowing at 1.5 SCFH for 4.5 hours. 6 parts by volume emulsion, 19 parts by volume water and 26 parts by volume tetrapropylene are collected. The temperature is reduced to 95° C. followed by addition of isobutylene via the submerged gas inlet tube at 6.5 SCFH for 5 hours, followed by nitrogen blowing at 1.5 SCFH for 2 hours at 100° C. The materials are cooled to room temperature and filtered with a diatomaceous earth filter aid.

Part II

A reactor equipped as described in Part II of Example 1 is charged with 2556 parts of the foregoing filtrate and 1250 parts xylene. The materials are heated to 40° C. followed by the addition of 72 parts 50% aqueous sodium hydroxide. Over a period of 1 hour at a temperature of 40°–60° C., 364 parts 37% aqueous formaldehyde are added in a dropwise fashion. The reaction mixture is heated to reflux and held at reflux for 3.5 hours. Following the reflux, water is removed as a xylene azeotrope with nitrogen blowing at 1.5 SCFH at a temperature up to 150° C. over a 2 hour period. The materials are vacuum stripped at 150° C. and 20 millimeters mercury. The materials are cooled to 90° C., the vacuum is released, and the residue is filtered with a diatomaceous earth filter aid. GPC analysis shows 81.8% by weight of the product has an $\overline{M}w$ of 672 and 18.2% by weight an $\overline{M}w$ of 291. Percent OH by Grignard analysis is 5.12% (5.9% theory).

EXAMPLE 3

Part I

To a reactor as described in Part I of the previous examples are charged 3456 parts of a 4-heptyl phenol. The materials are heated to 40° C. followed by addition of 240 parts Super Filtrol. The materials are dried by heating to 105°–110° C. with nitrogen blowing at 1.5 SCFH for 4.5 hours. The temperature is reduced to 95° C. and isobutylene is added via the submerged gas inlet tube at a rate of 6.5 SCFH over 5 hours. The materials are blown with nitrogen at 1.5 SCFH for 2 hours at 100° C., then cooled to room temperature. The materials are filtered at room temperature with a diatomaceous earth filter aid.

Part II

A reactor equipped as described in Part II of the previous examples is charged with 2331 parts of the foregoing product and 1250 parts xylene. The materials are heated to 40° C. followed by addition of 72 parts 50% aqueous NaOH. A total of 365 parts 37% aqueous formaldehyde is added dropwise over 1 hour at a temperature of 40°–60° C. The materials are heated to reflux and held at reflux for 3.5 hours. Water is removed as a xylene azeotrope with nitrogen blowing at 1.5 SCFH while heating to 150° C. over 2 hours followed by vacuum stripping at 150° C. at 20 millimeters mercury until substantially all xylene has been removed. The materials are cooled under vacuum to 90° C., the vacuum is released and the residue is filtered with a diatomaceous earth filter aid. GPC analysis shows a $\overline{M}w$ of 485 and hydroxyl analysis is 5.74 (6.40 theory).

EXAMPLE 4

Part I

To a reactor equipped as described in Part I of Example 1 are charged 2266 parts of a 4-tetrapropenyl phenol. The materials are heated to 40° C. followed by addition of 142 parts Super Filtrol. The temperature is increased to 100° C. at which time addition of 572 parts isobutylene is begun via the submerged gas inlet tube at a rate of 4 cubic feet per hour at 100° C. After isobutylene addition is completed, while the temperature is maintained at 100° C., the material is blown with nitrogen at 2 cubic feet per hour for 0.5 hours. The materials are cooled to 60° C. and filtered through a diatomaceous earth filter aid.

Part II

A reactor is charged with 1278 parts of the above reaction product and 212 parts of xylene. While stirring, 35 parts of 50% aqueous NaOH are added while the temperature increases exothermically to 39°–40° C. To this mixture is charged 71 parts of paraformaldehyde followed by slow heating to 150° C. while azeotroping water of reaction. The materials are then blown with nitrogen at 2 cubic feet per hour at a temperature of 120° C. followed by vacuum stripping to 150° C. at 20 millimeters mercury. The materials are cooled to 100 ° C. under vacuum then filtered through a diatomaceous earth filter aid. GPC analysis shows the filtrate contains 83.9% of material having $\overline{M}w$ of 719 and 16.1% having a $\overline{M}w$ of 281. Percent hydroxyl analysis is 5.1 (5.9 theory).

EXAMPLE 5

To a reactor equipped as described in Part I of Example 1 is charged 798 parts 4-tetrapropenyl phenol. The materials are heated to 40° C. wherein 50 parts Super Filtrol is added. The temperature is increased to 100° C. followed by addition of 202 parts isobutylene via the submerged gas inlet tube at 2 cubic feet per hour, followed by cooling to 40° C. Xylene (300 parts) is added, the material is stirred for 0.1 hours while heating to 50° C., then 56 parts paraformaldehyde are charged. The materials are heated to 150° C. while removing water via azeotropic distillation. The materials are vacuum stripped to 150° C. at 20 millimeters mercury, cooled under vacuum to 100° C. and filtered with a diatomaceous earth filter aid. GPC analysis shows 64.5% of the product has $\overline{M}w$ of 558 and 35.5% has $\overline{M}w$ of 301. Percent hydroxyl analysis is 4.1 (5.9 theory).

EXAMPLE 6

Part I

A reactor as described in Part I of Example 1 is charged with 3192 parts of 4-tetrapropenyl phenol. The materials are heated to 80° C. over 0.5 hours followed by the addition of 21 parts 93% sulfuric acid all at one time. The materials are heated to 85° C. over 0.1 hour at which time 1344 parts isobutylene are added via the submerged gas inlet tube at a rate of 3 SCFH over 3 hours while the temperature is maintained at 85°–91° C. The materials are held at 85° for 0.5 hours while nitrogen blowing at 2 SCFH. To this mixture is charged 6 parts calcium hydroxide followed by 12 parts water, the materials are heated to 130° C. with nitrogen blowing at 2 SCFH over 1.5 hours then vacuum stripped at 130° C. at 20 millimeters mercury for 0.5 hours. The materials are cooled to 90° C. under vacuum, vacuum is released and nitrogen is blown through the material at 2 SCFH. The residue is filtered with a diatomaceous earth filter aid. Analysis shows the product contains 99.3% by weight 2,6-di-t-butyl-4-PppPhOH.

Part II

To a reactor equipped as described in Part II of Example 1 is charged 1386 parts of the above-described material. The materials are heated at 135° C. for approximately 48 hours at which time analysis shows the materials contain 7.3% by weight 2,6-di-t-butyl-4-polypropylenephenol, 88.5% by weight 2-t-butyl-4-polypropylenephenol and 2.9% by weight of 4-polypropylene substituted phenol.

Part III

To another reactor is charged 970 parts of the heat treated material described in Part II of this example. The materials are heated to 35° C. with stirring, 5 parts 93% sulfuric acid is added, the materials are stirred for an additional 0.1 hour followed by dropwise addition over 0.2 hours of 140 parts 37% aqueous formaldehyde. The temperature is increased to 135° C., starting nitrogen blowing at 2 cubic feet per hour at 85° C., adding 200 parts xylene at the same time, to remove water by azeotropic distillation. The materials are then stripped to 150° C. at 20 millimeters mercury, 300 parts mineral oil are added and the solution is filtered with a diatomaceous earth filter aid. Analysis of the filtrate (GPC) shows 79.8% by weight has $\overline{M}w$ of 586 and 20.2% by weight $\overline{M}w$ of 338.

EXAMPLE 7

Part I

To a reactor equipped as described in Part I of Example 1, are charged 4788 parts 4-tetrapropenyl phenol. With nitrogen blowing at 1.5 cubic feet per hour the materials are heated to 75° C. at which time 88 parts 93% sulfuric acid are added. The temperature is increased to 85° C., then isobutylene is added via the submerged gas inlet tube for a period of 3 hours at 4 cubic feet per hour. While maintaining the temperature at 85° C., isobutylene addition is continued at the rate of 0.6 cubic feet per hour until a total of 1138 parts isobutylene are added.

Part II

To a reactor equipped as described in Part II of Example 1, are charged 94 parts phenol, 963 parts of the product from Part I, and 500 parts toluene. Over a period of 0.2 hours, 243 parts 37% aqueous formaldehyde are added in a dropwise fashion. The materials are heated to 135° C. and held at that temperature for 0.5 hours, removing water by azeotropic distillation. A portion of the toluene is removed and 120 parts mineral oil diluent are added. The temperature is reduced to 90° C. at which time 500 parts toluene and 22 parts 50% aqueous NaOH are added. The materials are heated to 135° C., removing water by azeotropic distillation. The toluene-containing solution is filtered at room temperature, followed by stripping to 140° C. with nitrogen blowing at 2 cubic feet per hour. GPC analysis shows 60.8% of the product has $\overline{M}w$ of 2501, 35.2% $\overline{M}w$ of 621 and 4% $\overline{M}w$ of 298. The product contains 6.2% hydroxyl by analysis.

EXAMPLE 8

Part I

To a reactor equipped as described in Part I of Example 1, are charged 5320 parts of 4-tetrapropenyl phenol. The materials are heated to 75° C. and 92 parts 93% sulfuric acid is charged. The temperature is increased to 85° C., then 1120 parts isobutylene are added at a rate of 3 cubic feet per hour for 5 hours, then at 0.5 cubic feet per hour for about 12 hours.

Part II

To a reactor equipped as described in Part I, are charged 2632 parts phenol. The materials are heated to 75° C., 50 parts 93% sulfuric acid are added, the temperature is increased to 85° C. followed by addition of 3136 parts isobutylene at a rate of 1.5–2 cubic feet per hour over 24 hours. The materials are then blown with nitrogen at 2 cubic feet per hour for 4 hours at 65° C. Analysis by thin layer chromatography indicates that the product contains 85.9% 2,4-di-t-butyl phenol.

Part III

To a reactor equipped as described in Part II of Example 1, is charged 963 parts of the product of Part I, 618 parts of the product of Part II and 1000 parts toluene. The materials are heated to 100° C. with nitrogen blowing at 2 cubic feet per hour. 243 parts 37% aqueous formaldehyde is added dropwise over 1.5 hours, the materials are heated to 120° C., held at that temperature for 4 hours, heated to 160° C., and held there for 3 hours. The materials are cooled, 525 parts mineral oil diluent are added followed by cooling to 50° C. Hexane (1000 parts) is added, the materials are stirred for 1 hour then 3 parts calcium hydroxide are added. The materials are heated to 80° C. with nitrogen blowing at 2 cubic feet per hour, holding at that temperature for 1 hour. The materials are cooled to room temperature and filtered. The filtrate is heated to 120° C. with nitrogen blowing at 2 cubic feet per hour to remove solvent. Before neutralization with calcium hydroxide and oil addition, GPC analysis shows 44.7% of the materials have $\overline{M}w$ of 683, 31.1% have $\overline{M}w$ of 375, 19.3% have $\overline{M}w$ of 243 and 4.9% have $\overline{M}w$ of 141.

EXAMPLE 9

Part I

To a reactor equipped as described in Part I of Example 1, are charged 6650 parts of 4-tetrapropenyl phenol. The materials are heated to 75° C. with nitrogen blowing at 2 cubic feet per hour, 115 parts 93% sulfuric are charged, followed by heating to 85° C. At 85° C., 1400 parts isobutylene are added at the rate of 1 cubic foot per hour for 22 hours.

Part II

To a reactor equipped as described in Example 1, Part II, are charged 418 parts 4-tetrapropenyl phenol, 324 parts of the reaction product described in Part II of Example 8, 504 parts of the product of Part I of this example and 500 parts toluene. The mixture is heated with stirring and nitrogen blowing at 2 cubic feet per hour to 100° C. Nitrogen blowing is then stopped and 191 parts 37% aqueous formaldehyde are added dropwise over 2 hours. The temperature is increased to 150° C. with nitrogen blowing at 1.5 cubic feet per hour. With stirring, 3 parts calcium hydroxide are added, stirring is continued for 1 additional hour with nitrogen blowing at 2 cubic feet per hour, 320 parts mineral oil diluent are added and the materials are stirred for an additional hour at 150° C. with nitrogen blowing at 2 cubic feet per hour. The materials are filtered through a diatomaceous earth filter aid. GPC analysis shows 97.9% have $\overline{M}w$ of 534 and 2.1% have $\overline{M}w$ of 142.

EXAMPLE 10

To a reactor equipped as described in Part II of Example 1, are charged 412 parts of the product described in Part II of Example 8, 1200 parts of 4-polyisobutene substituted phenol having an equivalent weight of 1200 and 700 parts toluene. At room temperature with stirring over a 0.7 hour period 162 parts 37% aqueous formaldehyde are added in a dropwise manner. A slight exotherm is observed. Heating is begun, removing water by azeotropic distillation at 110°–120° C. The materials are stripped to 150° C., 5 parts lime are added, the materials are stirred for 0.5 hours, the product is cooled to 100° C., 700 parts toluene are added and at 80° C. 700 parts hexane. The solution is filtered at room temperature. The filtrate is stripped to 120° C. with nitrogen blowing at 2 cubic feet per hour then vacuum stripped at 120° C. at 20 millimeters mercury. GPC analysis of the residue shows 82.9% have $\overline{M}w$ of 3682, 14.7% have $\overline{M}w$ of 366, 2.1% have $\overline{M}w$ of 215 and 0.3% have $\overline{M}w$ of 169. Grignard analysis shows the product contains 3.01% OH.

EXAMPLE 11

To a reactor as described in Part II of Example 1, are charged 642 parts of the reaction product described in Part II of Example 9, 1200 parts of 4-polyisobutene substituted phenol having equivalent weight of 1200 and 700 parts toluene. With stirring, over 0.7 hours, 162 parts 37% aqueous formaldehyde are added. A slight exotherm is observed. The materials are heated to 150° C. removing water by azeotropic distillation with nitrogen blowing at 1 cubic foot per hour. The materials are held at 150° C. for 1.5 hours with nitrogen blowing at 1 cubic foot per hour. Calcium hydroxide, 5 parts, are added and the materials are stirred for 0.5 hours at 150° C. followed by cooling to room temperature. While cooling, 1000 parts toluene and 500 parts hexane are added. The solution is filtered at room temperature, and the filtrate is stripped by heating to 150° C. with nitrogen blowing at 2 cubic feet per hour. GPC analysis of the residue shows greater than 95% of the product has $\overline{M}w$ of 2888. The product contains 3.02% OH (3.0% theory) by Grignard analysis.

EXAMPLE 12

To a reactor equipped as described in Part II of Example 1, are charged 966 parts of the product described in Part I of Example 7 and 600 parts toluene. Over 0.2 hours 159 parts benzaldehyde are added; the temperature rises from 22° C. to 30° C. The materials are heated to 135° C., removing water by azeotropic distillation. The materials are held at 135° C. for 2 hours with nitrogen blowing at 1 cubic foot per hour then cooled to 90° C. Calcium hydroxide, 10 parts, are charged and the materials are reheated to 145° C. with nitrogen blowing at 1.2 cubic feet per hour followed by vacuum stripping at 135°–145° C. and 20 millimeters mercury. The residue is filtered with a diatomaceous earth filter aid.

EXAMPLE 13

Part I

To a reactor equipped with a stirrer, thermometer, reflux condenser and gas inlet tube are charged 1410 parts dimerized decene (Brayco) having a bromine number of 55 and 1030 parts of 2,6-di-t-butyl phenol having a melting point of 52°–57° C. The materials are heated to 40° C., 122 parts Super Filtrol are added followed by heating at 95° C. for 3 hours, collecting water in a Dean-Stark trap, stripped to 90°–95° C. at 5 millimeters mercury pressure for 2.5 hours, heated at atmospheric pressure with nitrogen blowing to 145°–150° C., held at 145°–150° C. for 5 hours then stripped to 145°–150° C. at 5 millimeters mercury.

Part II

A reactor is charged with 582 parts of the product of Part I, 3.5 parts of para-toluene sulfonic acid, and 49 parts of 37% aqueous formaldehyde, adding the formaldehyde dropwise. The temperature is increased to 95° C. and the materials are refluxed at 95°–100° C. for 3 hours followed by stripping to 110° C. at 5 millimeters mercury. The residue is filtered through a diatomaceous earth filter aid.

EXAMPLE 14

Part I

A reactor is charged with 725 parts of polypropylene tetramer and 1030 parts of 2,6-di-t-butyl phenol described in Example 13. The materials are heated to 40° C. whereupon 88 parts Super Filtrol are added, nitrogen blowing at 0.5–1 cubic feet per hour is begun and the temperature is increased to 95° C. over 4 hours. Materials are stripped to 95° C. at 5 millimeters mercury, heated at atmospheric pressure with nitrogen blowing to 145° C., heated at 145°–150° C. for 5 hours, stripped to 145°–150° C. at 5 millimeters mercury, then filtered through a diatomaceous earth filter aid.

Part II

To a reactor are charged 450 parts of the filtrate from Part I, 80 parts benzaldehyde and 2.5 parts paratoluene sulfonic acid. Toluene, 250 parts is added, the materials are heated to 140° C. over 4.5 hours, collecting water in a Dean-Stark trap. The materials are stripped to 120° C. at 5 millimeters mercury pressure then cooled to room temperature. 52 parts mineral oil diluent are added, the mixture is heated to 140° C. and held at 140° C. for 2 hours. The oil solution is filtered with a diatomaceous earth filter aid. The filtrate contains 3.41% hydroxyl (4.45% theory) by analysis.

EXAMPLE 15

Part I

A reactor is charged with 2045 parts of a mixture of $C_{24}$–$C_{28}$ alpha olefins having a bromine number of 39.1 and 1030 parts of 2,6-di-t-butyl phenol described in Example 13. The materials are heated to 60° C., 154 parts Super Filtrol are added, heated to 85° C. with nitrogen blowing and held at 90°–95° C. for 9.5 hours until the infra-red spectrum showed no further change. The materials are stripped to 95° C. at 20 millimeters mercury.

Part II

A reactor is charged with 431 parts of the product of part I, 2.5 parts of para toluene sulfonic acid and 30 parts 37% aqueous formaldehyde. The materials are refluxed for 3 hours at 95°–100° C., stripped to 110° C. at 5 millimeters mercury pressure and filtered with a diatomaceous earth filter aid.

As indicated hereinabove, the products of this invention have utility as antioxidants for a wide variety of organic compositions. Such compositions include, but are not necessarily limited to, synthetic resins, including engineering plastics such as building construction materials and automobile parts, various elastomers, both synthetic and natural, oils, and fuels. The compounds of this invention have been found to be particularly valuable as antioxidants for use in lubricating oils and normally liquid fuels.

Lubricating oil compositions may be based on a wide variety of oils of lubricating viscosity including synthetic and natural oils. The compounds of this invention are used in lubricating oils in minor amounts, sufficient to improve the anti-oxidancy performance thereof. These amounts often range from about 0.1% to about 20%, frequently from about 0.2% to about 10%, and more often from about 0.3% to about 3%, all by weight. Lubricating compositions containing the compounds of this invention may also include additives designed to enhance other properties of the composition.

Lubricating oil compositions comprising the compounds of this invention are based on natural and synthetic lubricating oils and mixtures thereof. These lubricants include crankcase lubricating oils for spark-ignited and compression-ignited internal combustion engines, such as automobile and truck engines, marine and railroad diesel engines, and the like. Automatic transmission fluids, two-cycle engine lubricants, transaxle lubricants, gear lubricants, metal-working lubricants, hydraulic fluids and other lubricating oil and grease compositions can also benefit from the incorporation therein of the phenolic compounds of this invention.

In addition to the compounds of this invention, the use of other additives is contemplated.

It is frequently useful to incorporate, on an optional, as-needed basis, other known additives which include, but are not limited to, dispersants and detergents of the ash-producing or ashless type, auxiliary antioxidants, anti-wear agents, extreme pressure agents, emulsifiers, demulsifiers, foam inhibitors, friction modifiers, anti-rust agents, corrosion inhibitors, viscosity improvers, pour point depressants, dyes, lubricity agents, and solvents to improve handleability which may include alkyl and/or aryl hydrocarbons. These optional additives may be present in various amounts depending on the intended application for the final product or may be excluded therefrom.

The ash-containing detergents are the well-known neutral or basic Newtonian or non-Newtonian, basic salts of alkali, alkaline earth and transition metals with one or more hydrocarbyl sulfonic acid, carboxylic acid, phosphoric acid, mono- and/or dithio phosphoric acid, phenol or sulfur coupled phenol, and phosphinic and thiophosphinic acid. Commonly used metals are sodium, potassium, calcium, magnesium, lithium, copper and the like. Sodium and calcium are most commonly used.

Neutral salts contain substantially equivalent amounts of metal and acid. As used herein, the expression basic salts refers to those compositions containing an excess amount of metal over that normally required to neutralize the acid substrate. Such basic compounds are frequently referred to as overbased, superbased, etc.

Dispersants include, but are not limited to, hydrocarbon substituted succinimides, succinamides, carboxylic esters, Mannich dispersants and mixtures thereof as well as materials functioning both as dispersants and viscosity improvers. The dispersants include nitrogen-containing carboxylic dispersants, ester dispersants, Mannich dispersants or mixtures thereof. Nitrogen-containing carboxylic dispersants are prepared by reacting a hydrocarbyl carboxylic acylating agent (usually a hydrocarbyl substituted succinic anhydride) with an amine (usually a polyamine). Ester dispersants are prepared by reacting a polyhydroxy compound with a hydrocarbyl carboxylic acylating agent. The ester dispersant may be further treated with an amine. Mannich dispersants are prepared by reacting a hydroxy aromatic compound with an amine and aldehyde. The dispersants listed above may be post-treated with reagents such as urea, thiourea, carbon disulfide, aldehydes, ketones, carboxylic acids, hydrocarbon substituted succinic anhydride, nitriles, epoxides, boron compounds, phosphorus compounds and the like. These dispersants are generally referred to as ashless dispersants even though they may contain elements such as boron or phosphorus which, on decomposition, will leave a non-metallic residue.

Extreme pressure agents and corrosion- and oxidation-inhibiting agents include chlorinated compounds, sulfurized compounds, phosphorus containing compounds including, but not limited to, phosphosulfurized hydrocarbons and phosphorus esters, metal containing compounds and boron containing compounds.

Chlorinated compounds are exemplified by chlorinated aliphatic hydrocarbons such as chlorinated wax.

Examples of sulfurized compounds are organic sulfides and polysulfides such as benzyl disulfide, bis(chlorobenzyl)-disulfide, dibutyl tetrasulfide, sulfurized methyl ester of oleic acid, sulfurized alkylphenol, sulfurized dipentene, and sulfurized terpene.

Phosphosulfurized hydrocarbons include the reaction product of a phosphorus sulfide with turpentine or methyl oleate.

Phosphorus esters include dihydrocarbon and trihydrocarbon phosphites, phosphates and metal and amine salts thereof.

Phosphites may be represented by the following formulae:

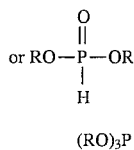

wherein each R is independently hydrogen or a hydrocarbon based group, provided at least one R is a hydrocarbon based group.

Phosphate esters include mono-, di- and trihydrocarbon-based phosphates of the general formula

Examples include mono-, di- and trialkyl; mono-, di- and triaryl and mixed alkyl and aryl phosphates.

Metal containing compounds include metal thiocarbamates, such as zinc dioctyldithiocarbamate, and barium heptylphenyl dithiocarbamate, molybdenum compounds, organodithiophosphate salts such as zinc, copper, manganese, etc., salts.

Boron containing compounds include borate esters and boron-nitrogen containing compounds prepared, for example, by the reaction of boric acid with a primary or secondary alkyl amine.

Viscosity improvers include, but are not limited to, polyisobutenes, polymethacrylate acid esters, polyacrylate acid esters, diene polymers, polyalkyl styrenes, alkenyl aryl conjugated diene copolymers, polyolefins and multifunctional viscosity improvers.

Pour point depressants are a particularly useful type of additive often included in the lubricating oils described herein. See for example, page 8 of "Lubricant Additives" by C. V. Smalheer and R. Kennedy Smith (Lesius-Hiles Company Publishers, Cleveland, Ohio, 1967).

Diluents include such materials as high boiling petroleum naphthas, mineral oil, etc. When used, they are typically present in amounts ranging from about 5% to about 50% by weight.

Antifoam agents used to reduce or prevent the formation of stable foam include silicones or organic polymers. Examples of these and additional anti-foam compositions are described in "Foam Control Agents" by Henry T. Kerner (Noyes Data Corporation, 1976), pages 125–162.

These and other additives are described in greater detail in U.S. Pat. No. 4,582,618 (column 14, line 52 through column 17, line 16, inclusive), herein incorporated by reference for its disclosure of other additives that may be used in the compositions of the present invention.

The components may be blended together in any suitable manner and then admixed, for example with a diluent to form a concentrate as discussed below, or with a lubricating oil, as discussed below. Alternatively, components can be admixed separately with such diluent or lubricating oil. The blending technique for mixing the components is not critical and can be effected using any standard technique, depending upon the specific nature of the materials employed. In general, blending can be accomplished at room temperature; however, blending can be facilitated by heating the components.

As previously indicated, the compositions of the present invention are useful as additives for lubricants. They can be employed in a variety of lubricant basestocks comprising diverse oils of lubricating viscosity, including natural and synthetic lubricating oils and mixtures thereof.

Natural oils include animal oils, vegetable oils, mineral lubricating oils, solvent or acid treated mineral oils, and oils derived from coal or shale. Synthetic lubricating oils include hydrocarbon oils, halo-substituted hydrocarbon oils, alkylene oxide polymers, esters of carboxylic acids and polyols, esters of polycarboxylic acids and alcohols, esters of phosphorus-containing acids, polymeric tetrahydrofurans, silicon-based oils and mixtures thereof.

Specific examples of oils of lubricating viscosity are described in U.S. Pat. No. 4,326,972 and European Patent Publication 107,282, both herein incorporated by reference for their disclosures relating to lubricating oils. A basic, brief description of lubricant base oils appears in an article by D. V. Brock, "Lubricant Base Oils" *Lubrication Engineering*, volume 43, pages 184–185, March, 1987. This article is herein incorporated by reference for its disclosures relating to lubricating oils. A description of oils of lubricating viscosity occurs in U.S. Pat. No. 4,582,618 (column 2, line 37 through column 3, line 63, inclusive), herein incorporated by reference for its disclosure to oils of lubricating viscosity.

The additives and components of this invention can be added directly to the lubricant. Preferably, however, they are diluted with a substantially inert, normally liquid organic diluent such as mineral oil, naphtha, toluene or xylene, to form an additive concentrate. These concentrates usually contain from about 10% to about 90% by weight of the components used in the composition of this invention and may contain, in addition, one or more other additives known in the art as described hereinabove. The remainder of the concentrate is the substantially inert normally liquid diluent.

The following Examples illustrate additive concentrates useful for preparing lubricating oil compositions. All parts and percentages are by weight and are given on an oil or diluent free basis except for the products of the preceding Examples in this specification which are not adjusted for diluent content.

EXAMPLE A

An additive concentrate for use in preparing lubricating oil compositions is prepared by blending 6.12 parts of a reaction product of ethylene polyamine with polyisobutenyl ($\overline{M}n$ approx. 1000) succinic anhydride, 3.67 parts of a magnesium alkyl benzene sulfonate having a metal ratio (metal to sulfonate equivalents) of 14.7, 7.41 parts of a calcium alkyl benzene sulfonate having a metal ratio of 20, 1.36 parts of glycerol monooleate, 3.47 parts of a zinc salt of mixed isobutyl-primary amyl dithiophosphate, 3.54 parts of a zinc salt of a mixed isopropyl-methylamyl dithiophosphate, 1.16 parts of an alkylated diphenyl amine, 13.61 parts of the product of Example 2, 0.07 parts of a kerosene solution of a silicone antifoam, 21.43 parts of a reaction product of an ethylene polyamine with polyisobutenyl ($\overline{M}n$ approx. 1700) succinic anhydride and 38.16 parts mineral oil diluent.

EXAMPLE B

An additive concentrate for use in preparing lubricating oil compositions is prepared by blending 18.27 parts of a reaction product of an ethylene polyamine with a polyisobutenyl ($\overline{M}n$ approx. 1700) succinic anhydride, 7.06 parts of an ethylene polyamine post treated polyester reaction product of pentaerythritol with polyisobutenyl (1000) succinic anhydride, 11.92 parts of a zinc salt of a mixed isopropyl-isooctyl dithiophosphate, 1.06 parts of nonyl phenoxy (polyethyleneoxy) ethanol, 3.27 parts of a magnesium alkyl benzene sulfonate having a metal ratio of 14.7, 5.30% of a calcium petroleum sulfonate having a metal ratio of 12, 0.05 parts of a kerosene solution of a silicone antifoam, 11.74 parts of the product of Example 2 and 41.38 parts of mineral oil diluent.

The following Examples illustrate lubricating oil compositions of this invention. All parts and percentages are by weight and are given on an oil-free basis except for the products of the preceding Examples in this specification which are not adjusted for diluent content.

EXAMPLE I

An engine lubricating oil composition contains 14.7% of the additive concentrate of Example A and 6.5% of an olefin copolymer viscosity improver (ECA 6911, Exxon) in a mineral oil basestock.

EXAMPLE II

An SAE 15W-40 engine lubricating oil composition contains 11.33% of the additive concentrate of Example B, 8.51% of an 8% in oil solution of a styrene-isoprene copolymer viscosity improver and 0.21% of a 40% in oil solution of a styrene-maleate copolymer reacted with aminopropyl morpholine in a mineral oil basestock.

EXAMPLE III

A 5W-30 engine lubricating oil composition contains 12.7% of an 8% in oil solution of a styrene-butadiene copolymer, 0.2% of a 40% in oil solution of a styrene-maleate copolymer reacted with aminopropyl morpholine and 11.71 parts of an additive concentrate made up of 23.06 parts of the reaction product of ethylene polyamine with polybutenyl ($\overline{M}w$ approx. 1700) succinic anhydride, 8.63 parts of the zinc salt of a mixed methylamyl-isopropyl dithiophosphoric acid, 0.68 parts of a copper salt of a mixed methylamyl-isopropyl dithiophosphoric acid, 0.85 parts of oleylamide, 5.55 parts of 2,6-di-t-butyl-4-tetrapropenyl phenol, 6.15 parts of an overbased sodium polybutenyl ($\overline{M}w$ approx. 1000) succinate, 1.45 parts of an overbased magnesium alkyl benzene sulfonate having a metal ratio of 14.7, 3.5 parts of the product of Example 7, 50.13 parts of mineral oil diluents and 0.07 parts of a kerosene solution of a silicone antifoam in a mineral oil basestock.

EXAMPLE IV

An SAE 80W-90 gear lubricating oil composition contains 0.02% of a kerosene solution of a silicone antifoam, 0.06% of a 40% in alkylated aromatic compound solution of an acrylic polyester, 0.04% of a styrene-maleate copolymer reacted with aminopropyl morpholine, and 10% of an additive concentrate containing 16.9 parts of a zinc salt of a mixture of 2-ethyl hexyl dithiophosphoric acid and 2-ethyl hexanoic acid, 10 parts of the product of Example 3, 5 parts of a borated $C_{16}$ alpha-olefin epoxide, 2.5 parts of the reaction product of polyisobutenyl ($\overline{M}w$ approx. 1000) succinic anhydride with N,N-diethylethanolamine, 30 parts of sulfurized isobutylene containing about 42% by weight of sulfur, 15.6 parts of a calcium overbased, polyisobutenyl ($\overline{M}w$ approx. 1000) succinic acid post treated, alkyl benzene sulfonic acid and 20 parts of mineral oil diluents in a mineral oil basestock.

EXAMPLE V

A hydraulic oil contains 10% of the product of Example 3 in a 500N mineral oil.

EXAMPLE VI

A 2-cycle engine lubricating oil composition contains 0.2% of a styrene-maleate copolymer pour point depressant (Hitec E-672, Ethyl), 0.01% of blue dye, 18% Stoddard Solvent and 10% of a product prepared substantially in accordance with the procedure of Example 2 in a mineral oil basestock.

EXAMPLE VII

A gear lubricating oil composition contains 0.02% of a kerosene solution of a silicone antifoam, 1% of a 40% in oil solution of a styrene-maleate copolymer reacted with aminopropylmorpholine and 7.5% of an additive concentrate containing 7.87 parts of a borated-reaction product of an ethylene polyamine with polyisobutenyl ($\overline{M}w$ approx. 1000) succinic anhydride, 15.46 parts of the reaction product of a methylamyl dithiophosphoric acid with propylene oxide which is reacted with phosphorus pentoxide and is neutralized with a $C_{11-14}$ tertiary alkyl primary amine (Primene 81R—Rohm and Haas), 13.33 parts of the product of Example 3, 1.33 parts of an 80% solution in a hydrocarbon solvent of the reaction product of dimercaptothiadiazole, formaldehyde and alkyl phenol, 4.67 parts of a 40% solution in a hydrocarbon solvent of an acrylic polyester antifoam, 1.33 parts of oleylamide, 0.36 parts of monoisopropanol amine, 48.67 parts of a sulfurized isobutylene containing about 42% by weight sulfur and 7.98 parts mineral oil diluent in a mineral oil basestock.

As indicated hereinabove, the compounds of this invention may be used as additives for normally liquid fuels.

The fuels used in the fuel compositions of this invention are well known to those skilled in the art and usually contain a major portion of a normally liquid fuel such as hydrocarbonaceous petroleum distillate fuel (e.g., motor gasoline as defined by ASTM Specification D-439-73 and diesel fuel or fuel oil as defined in ASTM Specification D-396). Fuels containing non-hydrocarbonaceous materials such as alcohols, ether, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Mixtures of fuels, such as mixtures of gasoline and alcohol, for example, methanol or ethanol, are among the useful fuels.

Examples of fuel mixtures are combinations of gasoline and ethanol, diesel fuel and ether, gasoline and nitromethane, etc. Particularly preferred is gasoline, that is, a mixture of hydrocarbons having an ASTM boiling point of 60° C. at the 10% distillation point to about 205° C. at the 90% distillation point.

Generally, these fuel compositions contain an amount of at least one compound of this invention sufficient to impart antioxidant and/or dispersant and detergent properties to the fuel; usually this amount is about 1 to about 10,000, preferably 4 to 1,000, more preferably 10 to 500, parts by weight of the compound per million parts by weight of fuel. Fuel compositions may also contain other additives which are well known to those of skill in the art. These may include ethers, such as ethyl-t-butyl ether, methyl-t-butyl ether and the like, alcohols such as ethanol and methanol, lead scavengers such as halo-alkanes (e.g., ethylene dichloride and ethylene dibromide), dyes, cetane improvers, antioxidants such as 2,6 di-tertiary-butyl-4-methylphenol, rust inhibitors, such as alkylated succinic acids and anhydrides, bacteriostatic agents, gum inhibitors, metal deactivators, demulsifiers, upper cylinder lubricants, anti-icing agents and the like. The invention is useful with lead-free as well as lead-containing fuels.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A process comprising reacting in the presence of an acidic catalyst at a temperature ranging from about 25° C. to about 200° C. a phenol or mixture of phenols of the formula

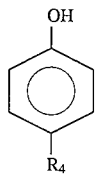

(II)

wherein at least 50% of the $R_4$ groups are aliphatic hydrocarbon groups containing at least 7 carbon atoms, with an olefin of the formula

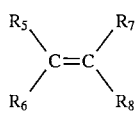

(III)

wherein each of $R_5$–$R_8$ is independently H or an alkyl group with the proviso that at least both of $R_5$ and $R_6$ or both of $R_7$ and $R_8$ are alkyl and the total number of carbon atoms in the olefin does not exceed 8, and wherein the molar ratio of (II) to (III) ranges from about 1:0.95 to about 1:1.2, and then reacting the product obtained thereby, in the presence of an acidic catalyst or a basic catalyst wherein the basic catalyst is selected from the group consisting of alkali and alkaline earth metal oxides, hydroxides and alkoxides, wherein the alkaline earth metal is selected from the group consisting of calcium, barium and strontium, with an aldehyde or ketone wherein the molar ratio of (II) to aldehyde or ketone ranges from about 2:1.8 to about 2:0.9 at temperatures ranging from about 25° C. to about 200° C., and recovering the product obtained thereby.

2. A process according to claim 1 wherein the acidic catalyst is neutralized following the reaction with the aldehyde or ketone.

3. A process according to claim 2 wherein the acidic catalyst is neutralized with a basic material selected from the group consisting of basic metal compounds, ammonia and amines.

4. A process according to claim 1 wherein the acid catalyst comprises sulfuric acid.

5. A process according to claim 1 wherein $R_4$ contains from 7 to about 100 aliphatic carbon atoms.

6. A process according to claim 1 wherein the olefin (III) is selected from isobutylene, isoamylene and diisobutylene.

7. A process according to claim 1 wherein the reaction with an aldehyde or ketone is with an aldehyde containing from 1 to about 4 carbon atoms.

8. A process according to claim 7 wherein the molar ratio of (II) to aldehyde ranges from about 2:0.95 to about 2:1.05.

9. A process according to claim 1 wherein the catalyst for the reaction with an aldehyde or a ketone is the basic catalyst.

10. A process according to claim 9 wherein the basic catalyst is an alkali metal hydroxide.

11. A process according to claim 1 wherein the molar ratio of (II) to aldehyde or ketone ranges from about 2:1.1 to about 2:0.95.

12. The process of claim 1 wherein from about 25% up to 50% of the $R_4$ groups are hydrogen.

13. A process comprising reacting in the presence of an acidic catalyst a phenol of the formula

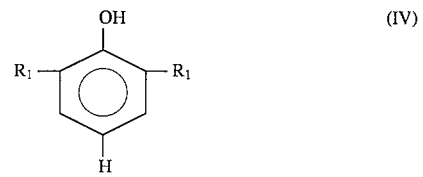

(IV)

wherein each $R_1$ is independently a tertiary alkyl group containing from 4 to about 8 carbon atoms with an olefin containing at least 7 carbon atoms to alkylate the phenol (IV) in the 4-position, then heating at an elevated temperature sufficient to cause partial dealkylation by removal of one $R_1$ group to form an intermediate reactant, and then reacting the intermediate obtained thereby, in the presence of an acidic catalyst or a basic catalyst wherein the basic catalyst is selected from the group consisting of alkali and alkaline earth metal oxides, hydroxides and alkoxides, and wherein the alkaline earth metal is selected from the group consisting of calcium, barium and strontium, with an aldehyde or ketone wherein the molar ratio of (IV) to aldehyde or ketone ranges from about 2:1.8 to about 20.9, at temperatures ranging from about 25° C. to about 200° C., and recovering the product obtained thereby.

14. A process according to claim 13 wherein each $R_1$ is a tertiary butyl group.

15. A process according to claim 13 wherein the olefin contains from 7 to about 100 aliphatic carbon atoms.

16. A process according to claim 13 wherein following the removal of one $R_1$ group the compound obtained thereby is reacted with an aldehyde.

17. A process according to claim 16 wherein the molar ratio of (IV) to aldehyde ranges from about 2:0.95 to about 21.05.

18. A process according to claim 13 wherein the catalyst is an acidic catalyst.

19. A process according to claim 18 wherein the acidic catalyst is neutralized following the reaction with the aldehyde or ketone.

20. A process according to claim 13 wherein the catalyst for the reaction with an aldehyde or a ketone is the basic catalyst.

21. A process according to claim 20 wherein the basic catalyst is an alkali metal hydroxide.

22. A process according to claim 13 wherein the molar ratio of (IV) to aldehyde or ketone ranges from about 2:1.1 to about 2:0.95.

23. The process of claim 13 wherein from about 25% to about 50 mole percent of the intermediate derived from the phenol (IV) is replaced with a phenolic compound of formula

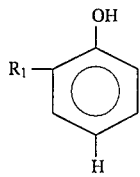

wherein the molar ratio of total phenolic compounds to aldehyde or ketone ranges from about 2:1.8 to about 2:0.9.

24. The process of claim 13 wherein from about 25 to about 50 mole percent of the intermediate derived from the phenol (IV) is replaced with an equivalent amount, based on % OH, of a compound having the formula

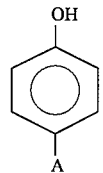

wherein A is H or hydrocarbyl and the molar ratio of total phenolic compounds to aldehyde or ketone ranges from about 2:1.8 to about 2:0.9.

* * * * *